United States Patent
Morgan et al.

[11] Patent Number: 5,834,784
[45] Date of Patent: Nov. 10, 1998

[54] LAMP FOR GENERATING HIGH POWER ULTRAVIOLET RADIATION

[75] Inventors: Gary L. Morgan, Elkridge, Md.; James M. Potter, Los Alamos, N. Mex.

[73] Assignee: Triton Thalassic Technologies, Inc., Ridgefield, Conn.

[21] Appl. No.: 850,143

[22] Filed: May 2, 1997

[51] Int. Cl.⁶ .................................................. G01N 21/00
[52] U.S. Cl. .......................................... 250/436; 250/435
[58] Field of Search .................................. 250/436, 437, 250/435; 315/248

[56] References Cited

U.S. PATENT DOCUMENTS

| | | | |
|---|---|---|---|
| 2,339,906 | 1/1944 | Barnes | 250/504 R |
| 3,943,403 | 3/1976 | Haugsjaa et al. | 315/248 |
| 4,101,424 | 7/1978 | Schooley et al. | 250/492.1 |
| 4,179,616 | 12/1979 | Coviello et al. | 250/436 |
| 4,266,167 | 5/1981 | Proud et al. | 315/248 |
| 4,336,456 | 6/1982 | Kuse et al. | 250/504 R |
| 4,427,922 | 1/1984 | Proud et al. | 315/248 |
| 4,427,923 | 1/1984 | Proud et al. | 315/248 |
| 4,427,924 | 1/1984 | Proud et al. | 315/248 |
| 4,427,925 | 1/1984 | Proud et al. | 315/248 |
| 5,013,959 | 5/1991 | Kogelschatz | 315/248 |
| 5,136,170 | 8/1992 | Gellert | 315/248 |
| 5,146,140 | 9/1992 | Piejak et al. | 315/248 |
| 5,194,740 | 3/1993 | Kogelschatz et al. | 315/248 |
| 5,343,114 | 8/1994 | Beneking et al. | 315/248 |
| 5,537,009 | 7/1996 | Chukanov | 315/248 |

*Primary Examiner*—Bruce Anderson
*Attorney, Agent, or Firm*—Martin Fruitman

[57] ABSTRACT

The apparatus is a gas filled ultraviolet generating lamp for use as a liquid purifier. The lamp is powered by high voltage AC, but has no metallic electrodes within or in contact with the gas enclosure which is constructed as two concentric quartz cylinders sealed together at their ends with the gas fill between the cylinders. Cooling liquid is pumped through the volume inside the inner quartz cylinder where an electrically conductive pipe spaced from the inner cylinder is used to supply the cooling liquid and act as the high voltage electrode. The gas enclosure is enclosed within but spaced from a metal housing which is connected to operate as the ground electrode of the circuit and through which the treated fluid flows. Thus, the electrical circuit is from the central pipe, and through the cooling liquid, the gas enclosure, the treated liquid on the outside of the outer quartz cylinder, and to the housing. The high voltage electrode is electrically isolated from the source of cooling liquid by a length of insulated hose which also supplies the cooling liquid.

9 Claims, 2 Drawing Sheets

LAMP FOR GENERATING HIGH POWER ULTRAVIOLET RADIATION

BACKGROUND OF THE INVENTION

The United States Government has certain rights to this invention under U.S. Department of Energy Contract No. W-7405-ENG-36.

This invention deals generally with the use of ultraviolet radiation to sterilize liquids and more specifically with a high power excimer lamp structure used to expose liquids to intense ultraviolet radiation to kill bacteria, even when the liquids are essentially opaque to ultraviolet radiation.

The exposure of liquids to ultraviolet radiation in order to sterilize them by killing bacteria is a long established technique. Many patents have been issued which are based on the ability of ultraviolet radiation to destroy bacteria, and such devices are common enough to be in use in many households and industries. Typically, such systems expose water to ultraviolet radiation by passing the water through an enclosure in which it is exposed to ultraviolet radiation.

One consideration which pervades all the prior art and is so well accepted that it is rarely even mentioned is that the treatment of water by exposure to ultraviolet radiation depends upon the water itself being significantly transparent to the ultraviolet radiation. The penetration of ultraviolet radiation through clear water typically may range from a few inches to more than a foot. Without such transparency to ultraviolet radiation, the purification of any liquid is very difficult because only the boundary of the liquid in actual contact with the source of radiation is affected by the radiation. Without the liquid's transparency to ultraviolet radiation, treatment requires very high intensity radiation and turbulence, so that the bacteria in the liquid can be killed in a very short time during which the turbulence assures that each portion of liquid is in direct contact with the ultraviolet radiation lamp.

However, achieving high intensity ultraviolet radiation is difficult. Traditional high intensity mercury lamps actually generate such a broad spectrum of radiation that the preferred wavelengths necessary to kill bacteria are only a small part of the power output. Moreover, conventional mercury lamps require an insulating sleeve over the lamp body which prevents direct contact between the lamp surfaces and the fluid being treated. On the other hand, excimer lamps, which have very narrow bandwidths at the appropriate wavelengths for sterilization of liquids, have been available only in relatively low power ratings. The historic limitations on the ultraviolet output power of existing excimer lamps have been rooted in their geometry.

Excimer lamps are essentially gas filled enclosures which are subjected to high voltage AC power by electrodes which are outside of, but in contact with, the enclosure. The lamp enclosures are constructed of a material such as quartz, so that they are transparent to ultraviolet radiation. When AC electrical power is applied, the lamp acts as the dielectric of a capacitor in which the electrodes are the plates of the capacitor, and, as in all capacitors, the dielectric provides all the impedance and uses all the power. For planar lamps, this means two metal electrodes are located in contact with the quartz gas filled planar envelope. For coaxial lamps, the envelope is usually formed of concentric cylinders sealed together at the ends, with the gas fill between the cylinders. The metal electrodes are then additional cylinders in contact with the outer surface of the outer quartz cylinder and inner surface of the inner cylinder.

Since existing lamps use one or more metal electrodes in contact with the lamp envelope, there is an inherent restraint on both lamp output and on lamp cooling. The electrode in contact with the outer surface of the lamp envelope has typically been a mesh which is partially transparent to ultraviolet radiation or a metal film which is so thin that some ultraviolet radiation passes through it. However, for high power operation such electrodes must also be capable of handling high electrical currents. That requires that they have significant volume in order to prevent limiting the electrical current or causing resistance heating. This high current requirement eliminates thin films and increases wire thickness in a mesh so greatly that the mesh blocks significant amounts of the ultraviolet radiation output. It then becomes a diminishing tradeoff in which the thick wire screens required for higher power levels block more of the ultraviolet radiation output which should be available for treatment of the liquid. Furthermore, the same mesh with large wires interferes with the cooling of the lamp surface, and when excimer lamps increase in temperature lamp efficiency and life are adversely affected.

The result has been an impasse which has prevented the use of excimer lamps in applications, such as the purification of opaque liquids, which require high ultraviolet radiation output.

SUMMARY OF THE INVENTION

The present invention overcomes the dilemma caused by using mesh electrodes when purifying liquids with high power ultraviolet radiation lamps by completely eliminating all the metal electrodes in contact with the lamp envelope. The excimer lamp of the invention is powered by high voltage AC, but has no metallic electrodes within or in contact with the envelope.

The lamp is constructed in the form of two concentric quartz cylinders sealed-together at their ends with the excimer gas fill between the cylinders. Cooling liquid is pumped through the central region inside the inner quartz cylinder where an electrically conductive pipe which is not in contact with the inner cylinder is used to supply this cooling liquid. Although it is not in contact with the inner quartz cylinder, this central pipe also acts as the high voltage electrode. A cable attaches the central pipe to a high voltage AC power source, but this high voltage electrode is electrically isolated from the source of cooling liquid by a suitably long length of electrically insulated tubing which also supplies the cooling liquid.

The entire lamp is enclosed within an outer metal cylindrical sheath which is also not in contact with the quartz envelope, but is connected to the return of the high voltage AC power source and is also grounded. The liquid to be treated flows through the metal sheath and over the outside surface of the external envelope of the excimer lamp.

The electrical circuit is dependent on the fact that the power applied to the lamp is alternating current, and, therefore, power can be transferred through capacitances. The two different liquid layers, cooling liquid inside the inner cylinder and treated liquid outside the outer cylinder, are the only electrical power feeds to the lamp and, although they theoretically have some conduction, they essentially act as capacitors to couple AC power to the excimer lamp. These liquid filled capacitors have little power loss because the liquids have high dielectric constants. Therefore, the capacitors formed by the liquid, and also the capacitors formed by the walls of the quartz envelope, result in impedances which are very much lower than that of the excimer gas within the lamp. Thus, virtually all the power is delivered to and used by the lamp.

Moreover, the liquid flowing within the central enclosure of the lamp and the treated liquid on the outside of the lamp are near perfect coolants for the quartz lamp envelope. Since there are no electrodes contacting the quartz envelope, the entire surface of the envelope is liquid cooled, and that liquid can be temperature controlled to establish the most desirable temperature for the quartz envelope. This temperature control is a major factor in securing long life operation for high power excimer lamps.

Finally, when the cooling liquid in the center of the lamp is selected to be a clear liquid, it also permits ultraviolet radiation emitted from the inner envelope of the lamp to pass through the cooling clear liquid and the other side of the lamp and to still reach the treated liquid on the far side of the lamp. In such a configuration, and unlike the situation in the traditional lamp with metal electrodes, there are no solid or mesh electrodes to absorb any of the ultraviolet radiation before it irradiates the liquid being treated.

The present invention thereby not only furnishes an ultraviolet radiation generating excimer lamp with high efficiency and long life, but there is no reason to believe that there is any inherent limit on its power capability.

DETAILED DESCRIPTION OF THE INVENTION

Figure 1:
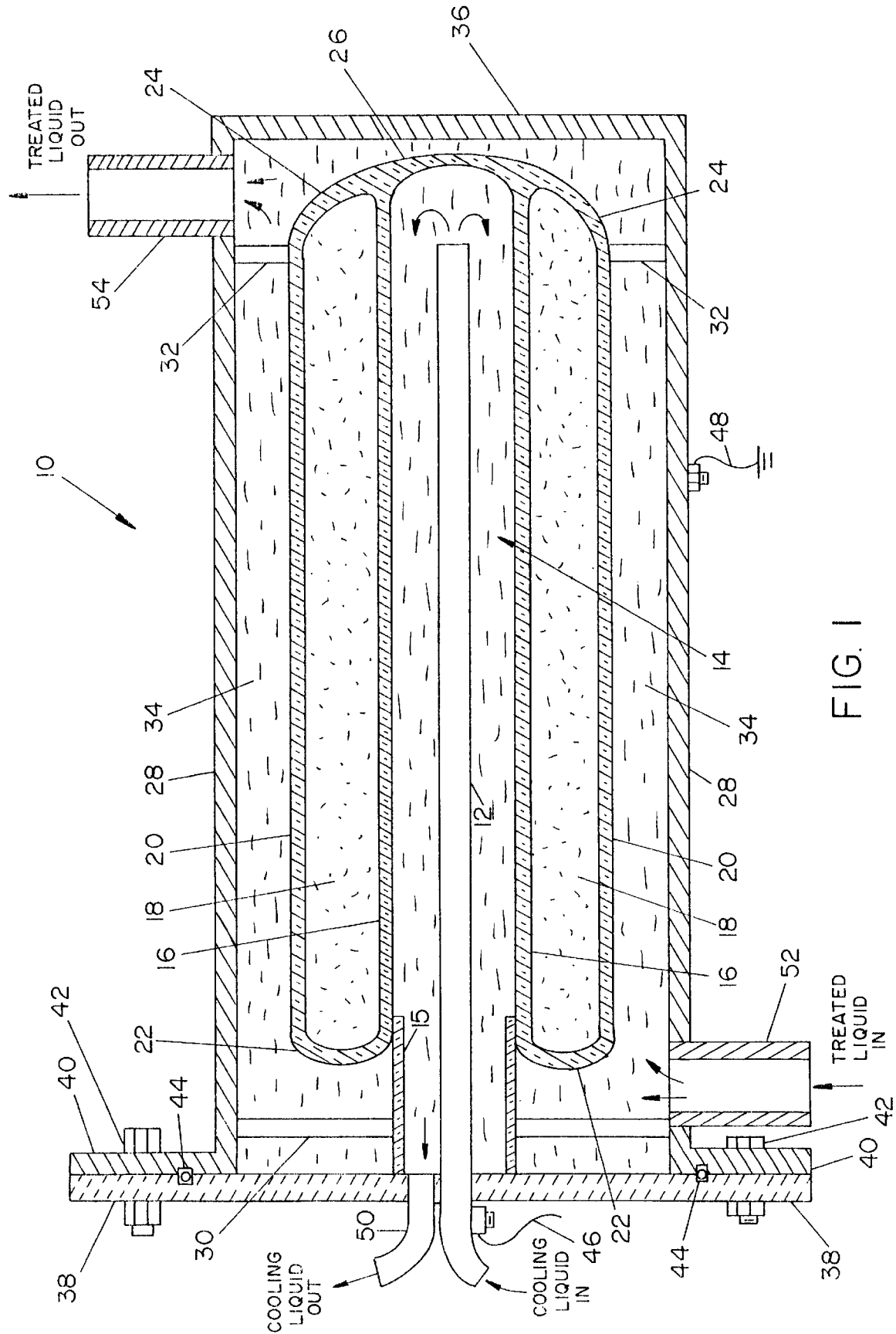
FIG. 1 is a cross section view across the liquid flow path of the excimer lamp of the preferred embodiment of the invention.

FIG. 1 is a cross section view along the liquid flow path of excimer lamp 10 of the preferred embodiment of the invention in which lamp 10 is constructed from multiple concentric cylinders. The internal cylinder is simple hollow metal pipe 12 through which liquid flows into volume 14 which is located around pipe 12. Volume 14 is essentially the volume enclosed by inner quartz cylinder 16 which is also one wall of excimer gas enclosure 18. Cylindrical sleeve 15 is an extension of inner quartz cylinder 16, closes off the end of volume 14, and helps maintain the position of inner quartz cylinder 16. Outer quartz cylinder 20 forms the outer wall of excimer gas enclosure 18. End walls 22 and 24 join inner quartz cylinder 16 and outer quartz cylinder 20 to complete excimer gas enclosure 18 and to form an annular space which is filled with excimer gas. End wall 24 is also extended to close off the end of inner quartz cylinder 16, thus also closing off remote end 26 of inner volume 14.

The actual operation of excimer gas filled enclosure 18 is the same as any conventional excimer lamp in that, when electrical energy is applied to the gas, micro-discharges within the gas generate ultraviolet radiation, with the wavelength of the radiation determined by the particular gas within gas enclosure 18.

The outermost cylinder is housing 28 and is held spaced away from outer quartz cylinder by supports 30 and 32. Supports 30 and 32 are among the several supports spaced around outer quartz cylinder 20 to center quartz cylinders 16 and 20 within housing 28 while maintaining volume 34 between housing 28 and outer quartz cylinder 20 open for the free flow of liquid through volume 34. Volume 34 is closed off at one end by end plate 36 which can either be an integral part of the cylinder of housing 28 as shown, or can be a removable cap bolted on in a manner similar to end plate 38 at the electrode connection end of lamp 10. End plate 38 is, however, constructed of an electrically insulating material such as plastic to electrically insulate central pipe 12 from housing 28. End plate 38 is held tight against plate 40 of housing 28 by bolts 42 and sealed by conventional "O" ring 44.

There are only two electrical connections to lamp 10. The high voltage connection is cable 46 attached to central pipe 12 and the return voltage and ground connection is a simple wire attached to housing 28. These connections can be made by any conventional means such as nuts on studs welded to the part to which the connection is made.

Liquid input and output connections are furnished for both cooling water and the liquid to be treated. Central pipe 12 serves to supply cooling water to volume 14. This cooling water flows out of pipe 12 near remote end 26 of volume 14, flows back along inner quartz cylinder 16 and sleeve 15, and leaves lamp 10 through outlet pipe 50. The liquid being treated enters the lamp through housing input pipe 52, flows along and around the outside of outer quartz cylinder 20 as it is irradiated by the ultraviolet radiation generated by the excimer discharge within excimer gas enclosure 18, and exits the lamp through housing outlet pipe 54.

In operation, as the treated liquid flows through lamp 10, the lamp appears electrically as a series of five dielectrics between the electrical inputs formed by pipe 12 and housing 28. Beginning at pipe 12, which is the high voltage connection and acts as one "plate" of the capacitor, the first dielectric is the cooling water within volume 14, the second dielectric is inner quartz cylinder 16, the third dielectric is the excimer gas within volume 18, the fourth dielectric is outer quartz cylinder 20, and the fifth is the treated liquid within volume 34. Housing 28, which is grounded for safety and is the return for the electrical power, acts as the other "plate" of the capacitor.

It is well understood that the impedance of any dielectric of a capacitor varies inversely with the dielectric constant of the material of the dielectric, so since water and quartz have high dielectric constants and the excimer gas has a low dielectric constant, the only high impedance in the series of dielectrics is the excimer gas. Thus, virtually all the electric power furnished by the power source is supplied to the excimer gas, while the liquids and the quartz serve essentially as connections to the dielectric of the excimer gas.

However, the liquids also serve another vital purpose. The liquids flowing across inner quartz cylinder 16 and outer quartz cylinder 20 cool the quartz walls of excimer gas enclosure 18 so that the excimer gas transfers its heat to the quartz walls and is also prevented from becoming overheated. Cooling the excimer lamp in this manner is vital to securing high reliability and long life for lamp 10.

Figure 2:
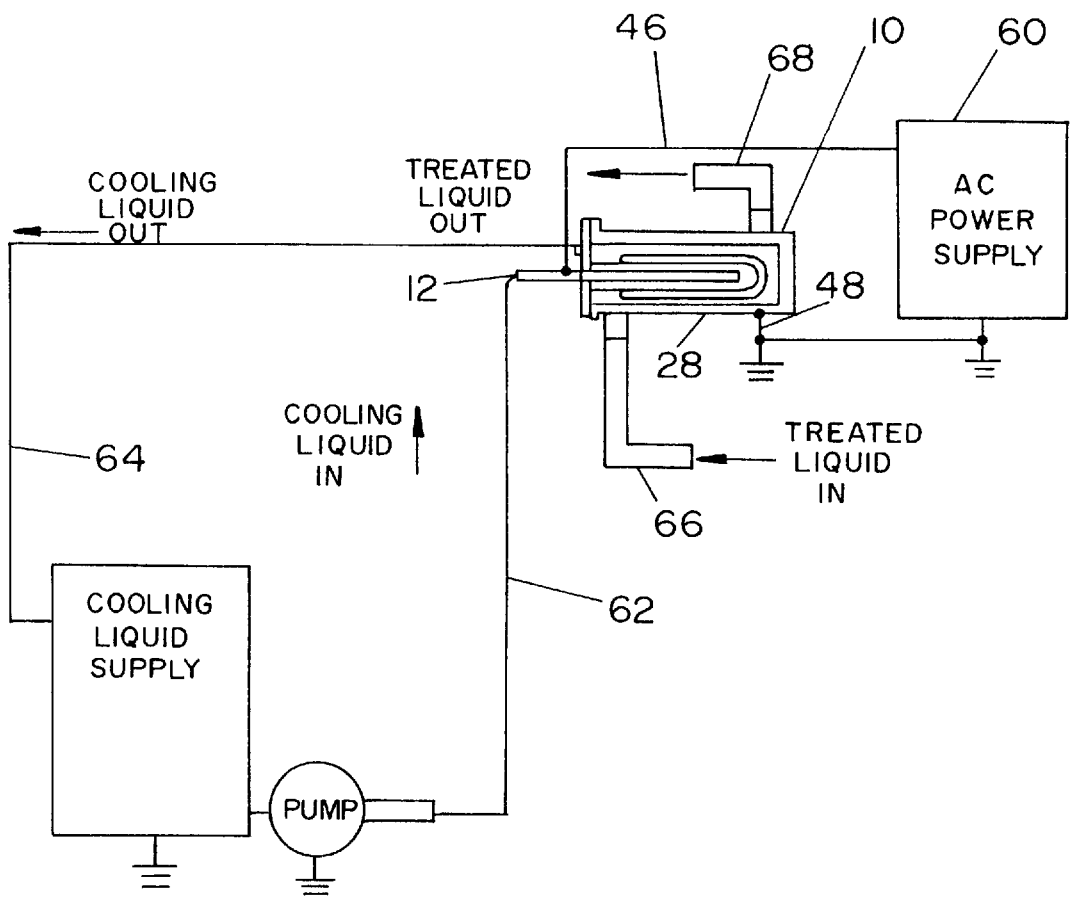
FIG. 2 is a simplified schematic diagram of the electrical and fluid flow arrangement of the invention.

FIG. 2 is a simplified schematic diagram of the electrical and fluid flow arrangement of the invention which depicts the means by which two liquid flow paths can be used in lamp 10 along with high voltage alternating current power supply 60.

As previously described, lamp 10 is fed cooling liquid through central pipe 12, but central pipe 12 is also connected to high voltage power supply 60 by cable 46. Conventional wisdom suggests that the source of the cooling liquid would have to be at the same high voltage as central pipe 12 or the power supply would be shorted out, but that is not actually the case.

If the cooling liquid feed path and return path to central pipe 12 are long enough and the impedance of the cooling liquid high enough, such liquid flow paths will merely act as high impedances in parallel with the lamp, and the load they cause on the power supply will be inconsequential. For instance, typical tap water has a resistivity in the range of 20 to 200 micromho, and therefore has a resistance of 150 kilohm to 1.5 megohm per foot when flowing in a 0.45 inch diameter plastic hose. It is then only necessary to determine what leakage current would be tolerable for power supply 60 and to make feed hose 62 for pipe 12 and return hose 64 long enough to limit the leakage current to that value.

As shown in both FIG. 1 and in FIG. 2, housing 28 of lamp 10 is actually electrically grounded, so there is no concern at all about any voltage being applied to it. Thus, treated liquid input pipe 66 and treated liquid outlet pipe 68 can be connected to any required equipment and handle liquid of any resistivity. However, in most anticipated applications even the liquid being treated has such a low conductivity that it would cause no difficulty even if it were used as the cooling liquid within the central portion of the lamp. This is actually a possibility is some applications because it would eliminate the need for a separate liquid supply for the cooling liquid, and even if the cooling liquid was opaque, the dimensions of the lamp could be designed to treat the cooling liquid as well. The preferred embodiment of the invention has been operated with the following structure, conditions, and results.

---

Housing (28) - material - stainless steel
length - 110 cm
Outer quartz cylinder (20) - wall thickness - 2.0 mm
length - 95 cm
Inner quartz cylinder (16) - wall thickness - 2.0 mm
length - 95 cm
Central liquid hoses (62)(64) - length - 1 meter
inside diameter - 1.2 cm
Central pipe (12) - material - stainless steel
inside diameter - 1.5 cm
length - 95 cm
Central liquid - tap water
Central liquid flow rate - 2 GPM
Treated liquid - 5% metal working fluid in water
Treated liquid flow rate - 150 GPM
Power supply (60) - 5 Kw
Excimer gas fill - Xenon/Bromine (dependent upon output wavelength desired, as well established in the literature)
Ultraviolet radiation output - 300 mw per square cm.
Bacteria kill rate - 3 log removal in 40 hours treating 600 gallons per lamp

---

The preferred embodiment of the described ultraviolet radiation generating lamp has operated in an industrial environment purifying opaque machine cutting fluids, and has operated for more than 1000 hours at full power output without failure.

It is to be understood that the forms of this invention as shown are merely preferred embodiments. Various changes may be made in the function and arrangement of parts; equivalent means may be substituted for those illustrated and described; and certain features may be used independently from others without departing from the spirit and scope of the invention as defined in the following claims.

For example, the configuration of lamp 10 need not be cylindrical, although that is simpler to construct. The lamp could be constructed of parallel planar sheets, in which case FIG. 1 would be a cross section view across a portion of such a configuration. Moreover, materials other than metal may be used for central pipe 12 and housing 28, as long as the materials are electrically conductive, and walls 16 and 20 of gas volume 14 may be constructed of materials other than quartz as long as the materials are transparent to ultraviolet radiation of the wavelength generated by the lamp. Furthermore, because most liquids have a dielectric constant greater than 10 and the invention is relatively independent of liquid conductivity, virtually all liquids are usable in this invention.

What is claimed as new and for which letters patent of the United States are desired to be secured is:

1. A radiation generating lamp comprising:

a housing forming a liquid tight outer enclosure with at least one electrically conductive wall, with the housing including. a treated liquid inlet and a treated liquid outlet;

a radiation generating gas enclosure located within the housing and spaced away from the electrically conductive walls of the housing, the gas enclosure including at least one wall which is transparent to radiation generated within the gas enclosure and at least one wall which is constructed of a dielectric material;

a gas filling the gas enclosure, with the gas capable of generating radiation when AC voltage is applied to the gas enclosure;

a liquid tight volume located within the housing so that the dielectric material wall of the gas enclosure serves as at least one wall of the volume, and the gas enclosure is located between the volume and the housing, with the volume including a cooling liquid inlet and a cooling liquid outlet;

an electrically conductive electrode located within the volume, penetrating a wall of the housing and a wall of the volume through electrical insulator means, and spaced away from the walls of the gas enclosure;

treated liquid flowing through the housing between the radiation transparent wall of the gas enclosure and the housing;

cooling liquid flowing through the volume between the electrode and the gas enclosure; and electrical connections attached to the housing and to the electrode whereby AC voltage is applied to the lamp.

2. The lamp of claim 1 wherein the housing, the gas enclosure, and the electrode are each of cylindrical configuration.

3. The lamp of claim 1 wherein the electrode is a hollow pipe which serves as the cooling liquid input.

4. The lamp of claim 1 wherein the housing is electrically grounded.

5. The lamp of claim 1 wherein all the walls of the gas enclosure are transparent to the radiation generated within the gas enclosure.

6. The lamp of claim 1 wherein the cooling liquid is transparent to the radiation generated within the gas enclosure.

7. The lamp of claim 1 wherein the cooling liquid inlet and the cooling liquid outlet are connected to a source of cooling liquid through lengths of electrically insulating hoses which are long enough to limit the leakage current through the hoses and through the liquid within them to a predetermined value.

8. The lamp of claim 1 wherein energy is capacitively coupled into the gas enclosure through liquid in the second volume and through liquid in the housing.

9. The lamp of claim 1 wherein the cooling liquid is tap water.

* * * * *